United States Patent
Johnson et al.

(10) Patent No.: US 11,074,459 B2
(45) Date of Patent: *Jul. 27, 2021

(54) PATIENT VIDEO MONITORING SYSTEMS AND METHODS FOR THERMAL DETECTION OF LIQUIDS

(71) Applicant: CareView Communications, Inc., Lewisville, TX (US)

(72) Inventors: Steven Gail Johnson, Highland Village, TX (US); Derek del Carpio, Corinth, TX (US); Kenneth W. Chapman, Lewisville, TX (US)

(73) Assignee: CareView Communications, Inc., Lewisville, TX (US)

( * ) Notice: Subject to any disclaimer, the term of this patent is extended or adjusted under 35 U.S.C. 154(b) by 13 days.

This patent is subject to a terminal disclaimer.

(21) Appl. No.: 16/732,499

(22) Filed: Jan. 2, 2020

(65) Prior Publication Data

US 2020/0151462 A1 May 14, 2020

Related U.S. Application Data

(63) Continuation of application No. 16/250,415, filed on Jan. 17, 2019, now Pat. No. 10,565,456, which is a (Continued)

(51) Int. Cl.
*G06K 9/00* (2006.01)
*C07C 1/00* (2006.01)
(Continued)

(52) U.S. Cl.
CPC ........ *G06K 9/00771* (2013.01); *A61B 5/0002* (2013.01); *A61B 5/145* (2013.01);
(Continued)

(58) Field of Classification Search
USPC ....... 382/100, 103, 106, 128–134, 155, 162, 382/168, 173, 181, 189, 194, 199, 209,
(Continued)

(56) References Cited

U.S. PATENT DOCUMENTS

| | | | |
|---|---|---|---|
| 7,146,211 B2 * | 12/2006 | Frei | A61B 5/316 607/2 |
| 8,211,035 B2 * | 7/2012 | Melker | G01N 33/497 600/532 |

(Continued)

*Primary Examiner* — Seyed H Azarian
(74) *Attorney, Agent, or Firm* — Meister Seelig & Fein LLP; Seth H. Ostrow, Esq.

(57) ABSTRACT

A system for monitoring a patient in a patient area having one or more detection zones, the system comprising one or more cameras, a user interface, and a computing system configured to receive a chronological series of frames from the one or more cameras, identify liquid candidates by comparing a current frame with a plurality of previous frames of the chronological series, determine locations of the liquid candidates, identify thermal signatures of the liquid candidates, determine types of liquids of the liquid candidates based on the locations and thermal signatures of the liquid candidates, and generate an alert with the user interface corresponding to the determined types of liquids.

18 Claims, 5 Drawing Sheets

Related U.S. Application Data continuation of application No. 15/926,416, filed on Mar. 20, 2018, now Pat. No. 10,217,004, which is a continuation of application No. 15/332,283, filed on Oct. 24, 2016, now Pat. No. 9,959,471.

(60) Provisional application No. 62/244,905, filed on Oct. 22, 2015, provisional application No. 62/261,810, filed on Dec. 1, 2015.

(51) Int. Cl.

| | |
|---|---|
| *A61B 5/145* | (2006.01) |
| *H04N 5/33* | (2006.01) |
| *A61M 5/168* | (2006.01) |
| *A61B 5/00* | (2006.01) |
| *H04N 5/247* | (2006.01) |
| *A61M 5/14* | (2006.01) |
| *A61B 5/02* | (2006.01) |
| *A61B 5/11* | (2006.01) |

(52) U.S. Cl.
CPC ...... *A61M 5/1689* (2013.01); *A61M 5/16886* (2013.01); *H04N 5/247* (2013.01); *H04N 5/33* (2013.01); *H04N 5/332* (2013.01); *A61B 5/02042* (2013.01); *A61B 5/1128* (2013.01); *A61B 5/6889* (2013.01); *A61B 2560/0242* (2013.01); *A61M 5/14* (2013.01); *G06K 2209/057* (2013.01)

(58) Field of Classification Search
USPC ....... 382/232, 254, 274, 286–291, 305, 312; 607/2; 378/21; 600/300, 322, 532; 340/573.1
See application file for complete search history.

(56) References Cited

U.S. PATENT DOCUMENTS

| | | | |
|---|---|---|---|
| 2009/0118594 A1* | 5/2009 | Zdeblick | A61M 1/1668 600/300 |
| 2009/0160656 A1* | 6/2009 | Seetharaman | A61B 5/412 340/573.1 |
| 2015/0119663 A1* | 4/2015 | Lim | A61B 5/150992 600/322 |

\* cited by examiner

PATIENT VIDEO MONITORING SYSTEMS AND METHODS FOR THERMAL DETECTION OF LIQUIDS

CROSS-REFERENCE TO RELATED APPLICATIONS

This application is a continuation of U.S. patent application Ser. No. 16/250,415, entitled "PATIENT VIDEO MONITORING SYSTEMS AND METHODS FOR THERMAL DETECTION OF LIQUIDS," filed on Jan. 17, 2019, which is a continuation of U.S. patent application Ser. No. 15/926,416, entitled "PATIENT VIDEO MONITORING SYSTEMS AND METHODS FOR THERMAL DETECTION OF LIQUIDS," filed on Mar. 20, 2018, issued as U.S. Pat. No. 10,217,004, which is a continuation of U.S. patent application Ser. No. 15/332,283, entitled "PATIENT VIDEO MONITORING SYSTEMS AND METHODS FOR THERMAL DETECTION OF LIQUIDS," filed on Oct. 24, 2016, issued as U.S. Pat. No. 9,959,471, which claims the priority of U.S. Provisional Application No. 62/244,905, entitled "PATIENT VIDEO MONITORING SYSTEMS AND METHODS FOR THERMAL DETECTION OF LIQUIDS," filed on Oct. 22, 2015, and U.S. Provisional Application No. 62/261,810, entitled "SYSTEM AND METHOD FOR PREDICTING PATIENT FALLS," filed on Dec. 1, 2015, the disclosure of which are hereby incorporated by reference in their entirety.

The present application is related to the following patents and applications, which are assigned to the assignee of the present invention:

a. U.S. Pat. No. 7,477,285, filed Dec. 12, 2003, entitled "Non-intrusive data transmission network for use in an enterprise facility and method for implementing,"
b. U.S. Pat. No. 8,471,899, filed Oct. 27, 2009, entitled "System and method for documenting patient procedures,"
c. U.S. Pat. No. 8,675,059, filed Jul. 29, 2010, entitled "System and method for using a video monitoring system to prevent and manage decubitus ulcers in patients,"
d. U.S. Pat. No. 8,676,603, filed Jun. 21, 2013, entitled "System and method for documenting patient procedures,"
e. U.S. Pat. No. 9,041,810, filed Jul. 1, 2014, entitled "System and method for predicting patient falls,"
f. U.S. application Ser. No. 12/151,452, filed May 6, 2008, entitled "System and method for predicting patient falls,"
g. U.S. application Ser. No. 14/039,931, filed Sep. 27, 2013, entitled "System and method for monitoring a fall state of a patient while minimizing false alarms,"
h. U.S. application Ser. No. 13/429,101, filed Mar. 23, 2012, entitled "Noise Correcting Patient Fall Risk State System and Method for Predicting Patient Falls,"
i. U.S. application Ser. No. 13/714,587, filed Dec. 14, 2012, entitled "Electronic Patient Sitter Management System and Method for Implementing,"
j. U.S. application Ser. No. 14/158,016, filed Jan. 17, 2014, entitled "Patient video monitoring systems and methods having detection algorithm recovery from changes in illumination,"
k. U.S. application Ser. No. 14/188,396, filed Feb. 24, 2014, entitled "System and method for using a video monitoring system to prevent and manage decubitus ulcers in patients,"
l. U.S. application Ser. No. 14/213,163, filed Mar. 13, 2014, entitled "System and method for documenting patient procedures,"
m. U.S. application Ser. No. 14/209,726, filed Mar. 14, 2014, entitled "Systems and methods for dynamically identifying a patient support surface and patient monitoring," and
n. U.S. application Ser. No. 14/710,009, filed May 12, 2015, entitled "Electronic Patient Sitter Management System and Method for Implementing."

The above identified patents and applications are incorporated by reference herein in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

The invention described herein generally relates to systems and methods for patient monitoring by analyzing video frames to gather medical information, and in particular, using multispectral including thermal sensors and imaging to detect liquids of a patient area that is being monitored.

Description of the Related Art

Healthcare facilities rely on patient monitoring to supplement interventions and reduce the instances of patient falls. Constant eyes-on monitoring of patients can be difficult for healthcare professionals to maintain. Video monitoring can be used to automate patient monitoring and increase the ability of a healthcare professional to effectively monitor a group of patients distributed between different rooms. Various systems and methods for patient video monitoring have been disclosed, such as U.S. Patent Application No. 2009/0278934 entitled System and Method for Predicting Patient Falls, U.S. Pat. No. 8,471,899 entitled System and Method for Documenting Patient Procedures, U.S. Pat. No. 8,675,059 entitled System and Method for Using a Video Monitoring System to Prevent and Manage Decubitus Ulcers in Patients, and U.S. Patent Application No. 2014/0092247 entitled System and Method for Monitoring a Fall State of a Patient and Minimizing False Alarms.

Elderly and sick patients are less agile and less responsive, so assistance is often needed in their daily chores. For example, a senior citizen with urinary incontinence may wear diapers to avoid wetting their pants or bed sheets, and a diaper must be changed immediately when soaking wet with urine. It is impossible for a patient to be always accompanied by a nurse. Moreover if a patient is verbally challenged, unconscious, or mentally dull due to a disease (e.g., a stroke), they may have problem informing the nurse immediately when in need of a diaper change. Once a delayed diaper change becomes the norm, not only will the patient feel very uncomfortable, but also other diseases such as diaper rash may occur.

Another area of concern in a healthcare facility setting includes monitoring intravenous (IV) liquids. Physicians and other medical personnel may apply IV delivery system to administer medical solutions to patients intravenously. For safety reasons and in order to achieve optimal results, it is desirable to administer IV liquids in accurate amounts as prescribed by the physician and in a controlled fashion. It is unfortunately the case that in many circumstances, depletion of and improper delivery of IV liquids can go unnoticed by hospital personnel for relatively lengthy periods. This is because it is not feasible for medical establishments to routinely provide personnel who can continuously monitor each and every IV infusion procedure that the medical establishment undertakes. There is a need for systems and methods that can automatically detect and monitor the status of liquids within a patient area to alert and summon a healthcare professional to intervene when events are detected.

SUMMARY OF THE INVENTION

The present invention provides a system and method for monitoring a patient in a patient area having one or more detection zones. The system comprising one or more cameras, a user interface, and a computing system configured to receive a chronological series of frames from the one or more cameras, identify liquid candidates by comparing a current frame with a plurality of previous frames of the chronological series, determine locations of the liquid candidates, identify spectral, including thermal signatures of the liquid candidates, determine types of liquids of the liquid candidates based on the locations and thermal signatures of the liquid candidates, and generate an alert with the user interface corresponding to the determined types of liquids.

The computing system may be configured to determine a difference between spectral responses and temperatures and positions of pixels in the current frame and spectral responses and temperatures and positions of pixels in the plurality of previous frames to identify groups of pixels as the liquid candidates. The computing system can distinguish the groups of pixels from a background of the current frame using at least one of edge detection, motion detection, and thermal and spectral properties.

In certain embodiments, the computing system may be configured to determine presence of intravenous (IV) liquids and bodily fluids from the liquid candidates based on the locations and spectral, including thermal signatures of the liquid candidates. The computing system can determine that the liquid candidates are IV liquids. In one embodiment, the computing system is configured to determine that the liquid candidates are IV liquids based on determining at least one of: the liquid candidates' distance from a patient, the liquid candidate having a uniform temperature of less than or equal to room temperature or with other spectral difference, a depletion of the liquid candidates, drip activity motion, and presence of an IV line from the liquid candidate to the patient. The computing system may further determine depletion of the IV liquids. The computing system may determine the depletion of the IV liquids by determining volumes of the IV liquids. In a further embodiment, the computing system is configured to determine volumes of the IV liquids in the current frame, determine volumes of the IV liquids in the plurality of previous frames, compare the volumes of the IV liquids in the current frame to the volumes of the IV liquids in the plurality of previous frames, determine a rate of change of the IV liquids, and determine an estimate of when the depletion of the IV liquids will occur.

According to another embodiment, the computing system is configured to determine that the liquid candidates are bodily fluids. The computing system may be configured to determine that the liquid candidates are bodily fluids based on an identification of a warm substance near the patient. In yet another embodiment, the computing system is configured to determine that the liquid candidates are bodily fluids based on a dispersion pattern.

The method comprises receiving a chronological series of frames from one or more cameras, identifying liquid candidates by comparing a current frame with a plurality of previous frames of the chronological series, determining locations of the liquid candidates, identifying thermal signatures of the liquid candidates, determining types of liquids of the liquid candidates based on the locations and thermal signatures of the liquid candidates, and generating an alert with a user interface corresponding to the determined types of liquids.

In one embodiment, the method further comprises determining a difference between temperatures, spectral responses, and positions of pixels in the current frame and temperatures, spectral responses, and positions of pixels in the plurality of previous frames to identify groups of pixels as the liquid candidates. The groups of pixels may be distinguished from a background of the current frame using at least one of edge detection, motion detection, thermal, and spectral properties. The method may further comprise determining a presence of intravenous (IV) liquids and bodily fluids from the liquid candidates based on the locations and thermal or spectral signatures of the liquid candidates.

According to another embodiment, the method may further comprise determining that the liquid candidates are IV liquids. The liquid candidates may be determined as IV liquids based on determining at least one of: the liquid candidates' distance from a patient, the liquid candidate having a uniform temperature of less than or equal to room temperature, a depletion of the liquid candidates, drip activity motion, and presence of an IV line from the liquid candidate to the patient. In yet another embodiment, the method may further comprise determining that the liquid candidates are bodily fluids. The liquid candidates may be determined as bodily fluids based on an identification of a warm substance near the patient.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE INVENTION

Figure 1:
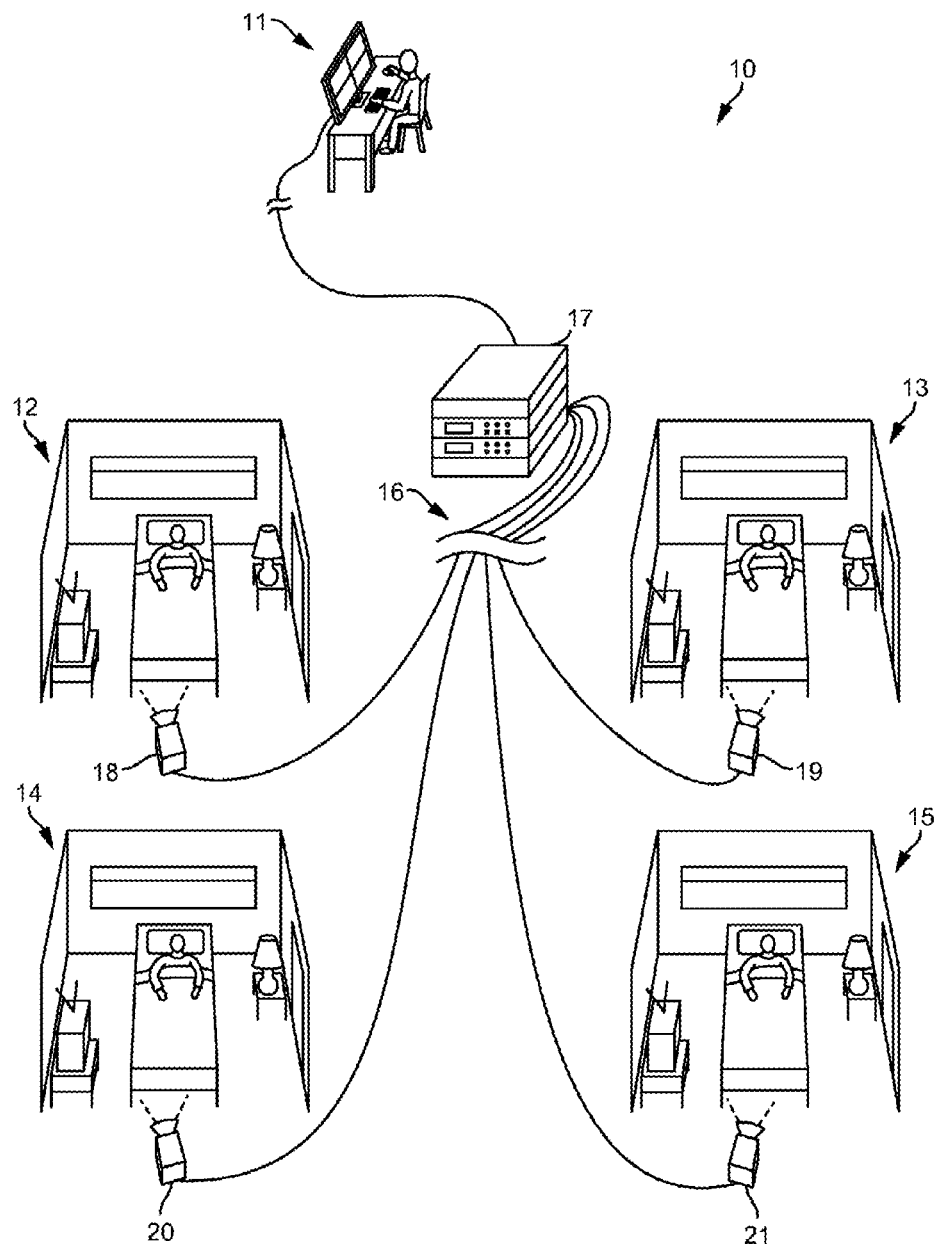
FIG. 1 illustrates a monitoring system according to an embodiment of the present invention.

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

For simplicity, certain terms will be used synonymously throughout the specification and in the claims. For instance, the term "liquid" is generally intended to include bodily fluids such as blood and urine, liquids in intravenous systems, and in some cases beverages. Likewise, for inclusiveness, personnel with responsibility for or duty to a patient or resident will be generally referred to as a healthcare facility (HCF) staff, professionals or both, regardless of whether that person's vocation is that of a physician, nurse, therapist, aide (or nurses' aid), administrator or any other type of healthcare worker that interacts with the patient or resident for the purposes of providing or facilitating a healthcare service. It should, however, be appreciated that given the nature of certain aspects of the present invention, that the HCF staff may not necessarily be present on the facility campus but may be present at a remote site, such as an office for a physician, insurance compliance agent, lawyer, facility manager, etc.

Additionally, the description of the present invention is better understood in relation to certain events that may or may not occur based on the detection and analysis of liquids within the patient area. These events may be memorialized videographically, on individual video frames, sequences of video frames or some combination of the two. While the present invention will be described largely with respect to a video frame or frames, a single video frame may contain additional information such as audio and annotated information, either manually input or derived automatically by the system, timestamps, etc., or alternatively a group of video frames may be collected as a file of related data that also contains additional related information, i.e., audio, annotated information, timestamps, etc. A frame may comprise a plurality of channels such as red, green, blue (RGB), infrared (IR), and other specific visible and non-visible spectral band channels. Still further, the term "healthcare facility" will be used synonymously with any facility in which the patient/resident receives medical treatment such as a hospital, clinic, nursing home, long term care facility (typically a facility for treating specialized ailments other than age, such as severely disabled or paraplegic patients, comatose patients, end-of-life patients, etc.) and may in fact extend to the assisted living facilities and patient's home or residence in cases in which ongoing care is provided in a non-hospital patient/resident setting (such as for hospice and care for Alzheimer's victims).

Various embodiments of the present disclosure concern video monitoring using multispectral and/or thermal sensors and imaging to detect patient events related to a presence (or lack) of liquids within a patient area. Such events can concern situations in which a patient is at increased risk or otherwise is in need of intervention. Patient events can include patient vomiting, defecation, urination, hemorrhaging, sweating, as well as spills and exhaustion of IV liquids, among various other events. Thermal imaging, also known as thermography, is a technique for producing an image of invisible infrared light emitted by objects with the use of a thermal imaging camera. Multispectral imaging is a superset of thermal imaging and may be defined as technique for capturing image data at specific frequencies across the electromagnetic spectrum. The multispectral and/or thermal imaging camera is operable to produce an image showing the temperature differences of a surface. Images from the multispectral or thermal imaging camera may then be interpreted to detect liquids. Multispectral and thermal sensors and imaging may be incorporated into an HCF's surveillance system for identifying the patient events, monitoring them with surveillance audio/video ("A/V") data, alerting HCF staff of the patient events, and saving the surveillance A/V files to a storage device, along with corresponding identification data, for future retrieval.

Moreover, as will be discussed below, embodiments of the present monitoring system operates autonomously, without manual intervention. Using the exemplary surveillance system, the workload on the HCF staff can be significantly and immediately reduced through the implementation of a semi-autonomous patient monitoring system by using and analyzing video surveillance data in accordance with exemplary embodiments of the present invention. Here, the aim is to reduce the overall workload on the HCF staff professionals, while simultaneously creating a succinct video record of patient events by using multispectral and/or thermal imaging techniques with the video monitoring system. The presently described system and method for using a video monitoring system to detect liquids in patient areas greatly reduces the amount of manual intervention required from an attending HCF staff member by automatically detecting the presence and volume of certain liquids. Additionally, the video record may be automatically annotated with relevant patient event information, timestamps, HCF staff comments and verifications and archived to locations secure from unauthorized alterations. These processes run largely in the background until and unless the system determines that intervention by the HCF staff is warranted.

FIG. 1 is a schematic diagram of a patient monitoring system 10. The patient monitoring system 10 can allow a healthcare professional to monitor multiple patient areas 12-15 from a monitoring station 11 via a computing system 17. The monitoring station 11 can comprise a user interface, which can include a screen and an input. The screen can display images of the patient areas 12-15, indications of one or more states of the patients being monitored, patient data, and/or other information. In some embodiments, the components of the monitoring station 11 are portable such that the monitoring station 11 can move with the healthcare processional.

While four patient areas 12-15 are shown in FIG. 1, any number of patient areas can be monitored at the monitoring station 11 via the computing system 17. The monitoring station 11 can be remote from the patient areas 12-15. For example, the monitoring station 11 can be on the same or different floor as the patient area 12-15, in the same or different building as the patient area 12-15, or located in a geographically different location as the patient area 12-15. Furthermore, the patient areas 12-15 can be remote from each other. The computing system 17 can be in one particular location or the components of the computing system 17 can be distributed amongst multiple locations. The computing system 17 can be at the monitoring station 11 or can be remote from the monitoring station 11 and/or the patient areas 12-15.

As shown in FIG. 1, a plurality of cameras 18-21 can be respectively positioned to view and generate frames of the plurality of patient areas 12-15. Information concerning the frames, such as analog or digital encodings of the frames, can be transmitted from the plurality of cameras 18-21 along data channels 16 to the computing system 17. In some cases, the computing system 17 is a single unit, such as a server, a personal computer (e.g., a desktop computer or a laptop computer), or a mobile computing device (e.g., smart phone, tablets, etc.). In some cases, the computing system 17 is distributed amongst several units, such as one or more personal computers, one or more mobile computing devices, one or more servers, circuitry within one or more of the cameras 18-21, and/or other computing devices. In some cases, the computing system 17 is part of a cloud computing network. The data channels 16 can be wired lines of a network (e.g., a local area network) and/or wireless channels (e.g., Wi-Fi or cellular network). The network may be any suitable type of network allowing transport of data communications across thereof. In other embodiments, the network may be the Internet, following known Internet protocols for data communication, or any other communication network, such as any wide area network (WAN) connection, or any combination thereof.

Each of the plurality of cameras 18-21 can generate a chronological series of frames (e.g., as images). The plurality of cameras 18-21 can be analog or digital cameras. Each of the plurality of cameras 18-21 can capture a sequence of frames at a predetermined frame rate, such as six, eight, sixteen, twenty-four, or some other number of frames per second. The resolution of digital cameras is usually defined by the number of pixels both horizontally and vertically (such as 640×480) or as a total number of pixels in the image (such as 1.4 mega pixels), while the resolution of analog video cameras is typically defined by the number of television lines. Analog frames can be converted to digital frames by analog-to-digital conversion circuitry (e.g., as part of the computing system 17 and/or the plurality of cameras 18-21). The plurality of cameras 18-21 can have infrared illumination or night vision capabilities for operating in low light conditions. According to one embodiment, the plurality of cameras 18-21 may include a multispectral or thermographic camera (or thermal imaging camera) capable of producing a thermal image of objects using infrared, or other non-visible or visible spectral, radiation.

Figure 2:
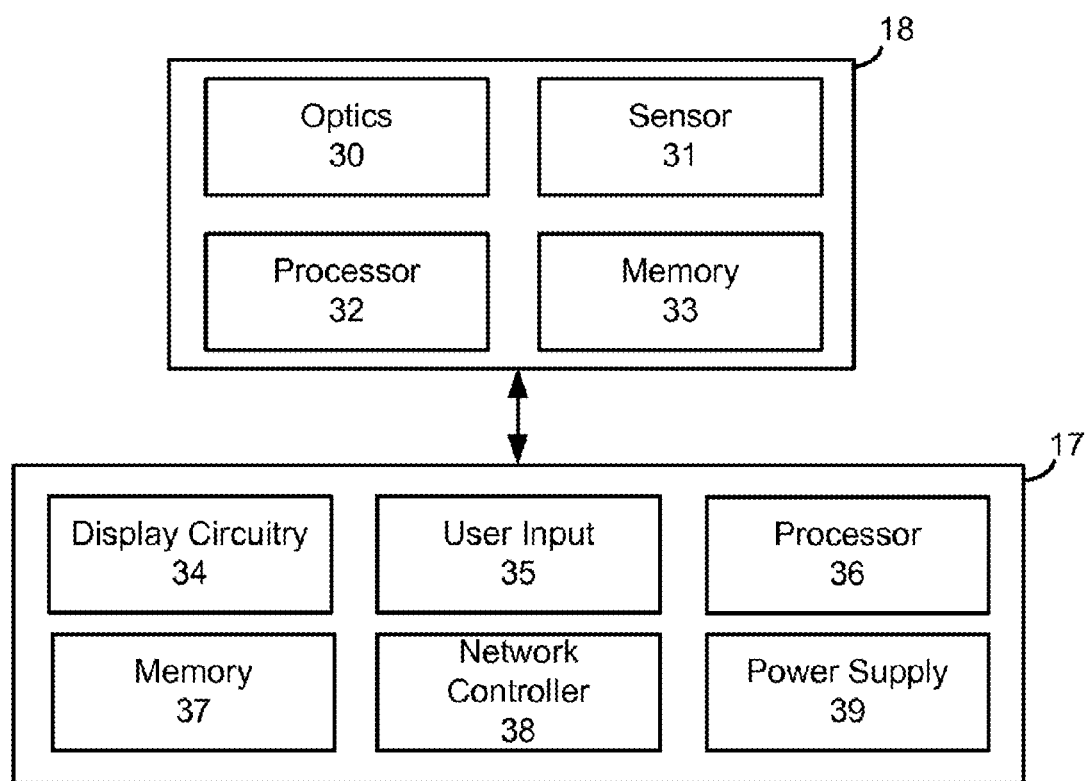
FIG. 2 illustrates a block diagram of components of a monitoring system according to an embodiment of the present invention.

FIG. 2 shows a block diagram of circuitry of the monitoring system 10. Although camera 18 is specifically shown as an exemplar, the components of the camera 18 can be included as part of each camera and the monitoring system 10. The camera 18 can include optics 30. Optics 30 can include a lens, a filter, and/or other components for capturing and conditioning the light of the patient area. The camera 18 can further include a sensor 31 for converting light from the optics 30 into electronic signals. Different types of sensors 31 can be used depending on whether the camera 18 is analog (e.g., generating analog video) or digital (e.g., generating discrete digital frames). The sensor 31 can include a charge-coupled device (CCD), a complementary metal-oxide-semiconductor (CMOS), or a specialized thermal imaging focal plane array (FPA) image sensing device.

The camera 18 can further include a processor 32 and memory 33. The processor 32 can perform various computing functions, such as those described herein or otherwise useful for operating the camera 18. The memory 33 can be a non-transient computer readable storage medium (e.g., random access memory or flash) for storing program instructions and/or frames. For example, the processor 32 can be configured to execute program instructions stored on the memory 33 for controlling the camera 18 in converting visible or non-visible light from the patient area 12 into digital signals with the sensor 31, storing the digital signals on the memory 33 as frame data, transferring the frame data to the computing system 17, and/or performing any other function. The processor 32 may perform various signal conditioning and/or image processing on the frames. The processor 32 may include a dedicated video processor for image processing. Although not illustrated, the camera 18 can further include a network interface controller and a power supply. The camera 18 may include a user interface which can include user controls and/or an audible alarm.

The computing system 17 can comprise a single housing or multiple housings among which circuitry can be distributed. The computing system 17 can include display circuitry 34 which can provide a graphics output to a screen. Display circuitry 34 can include a graphics processor and graphics memory which can support user interface functionality. Display circuitry 34 may be part of a separate display, such as a screen, handheld device, or remote terminal. Display circuitry 34 can facilitate the display of frames taken by the camera 18 of the patient area 12 on a screen and/or patient status information. User input circuitry 35 can include components for accepting user commands such as a keyboard, mouse, trackball, touchpad, touch screen, joystick, slider bar, or any other control. User input circuitry 35 can facilitate the definition of boundaries and monitoring zones, as will be further described herein.

The computing system 17 can include a processor 36 and memory 37. The memory 37 can be one or more discrete non-transient computer readable storage medium components (e.g., RAM, ROM, NVRAM, EEPROM, and/or FLASH memory) for storing program instructions and/or data. The processor 36 can be configured to execute program instructions stored on the memory 37 to control in the computing system 17 in carrying out the functions referenced herein. The processor 36 can comprise multiple discrete processing components to carry out the functions described herein as the processor 36 is not limited to a single processing component. The computing system 17 can include a network controller 38 for facilitating communication with the cameras 18-21 and/or other remote components. The computing system 17 can include a power supply 39 which can facilitate a connection to an electrical outlet and/or the power supply 39 can comprise a battery. Whether distributed or unified, the components of the computing system 17 can be electrically connected to coordinate and share resources to carry out functions.

Figure 3:
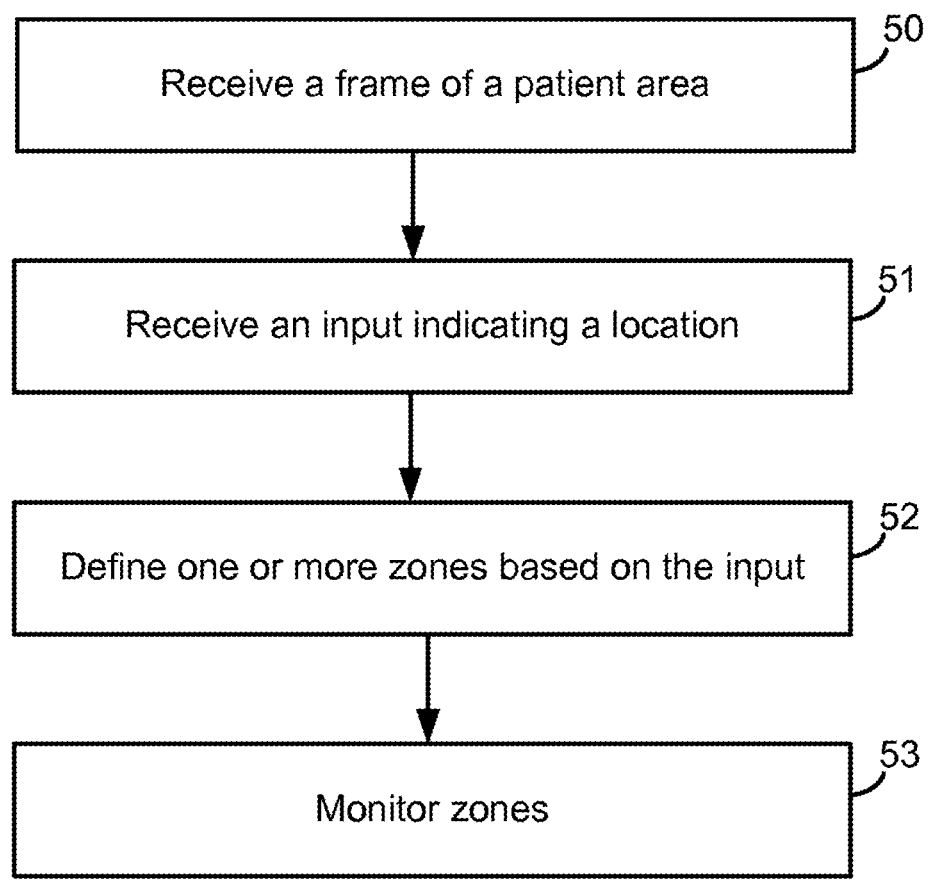
FIG. 3 illustrates a flowchart of a method for initializing a monitoring system according to an embodiment of the present invention.

FIG. 3 illustrates a flow chart of a method for setting up a monitoring system to monitor a patient. The method includes receiving 50 a frame of a patient area. The frame can be an image generated by the camera 18 and can be received 50 by the computing system 17 of FIGS. 1-2. The frame can be displayed on a screen at the monitoring station 11. The patient area can correspond to any area associated with a patient and/or where IV liquids may be present. Such areas can include a bed, bedside, IV stand, a chair, a wheelchair, a bed pan, etc.

The method can further include receiving 51 an input indicating a location. The input may be provided by a healthcare professional at the monitoring station 11 with a user interface. The indicated location can correspond to an area occupied by the patient and/or IV delivery system. In some cases, a healthcare professional can indicate one or more boundaries associated with the patient and IV delivery system, such as the left and right sides of a bed. For example, the healthcare professional can designate the left side and the right side of the bed 60 shown in FIG. 4. It is noted that patient areas may be automatically identified through a pattern recognition procedure implemented in the monitoring system in some embodiments.

Figure 4:
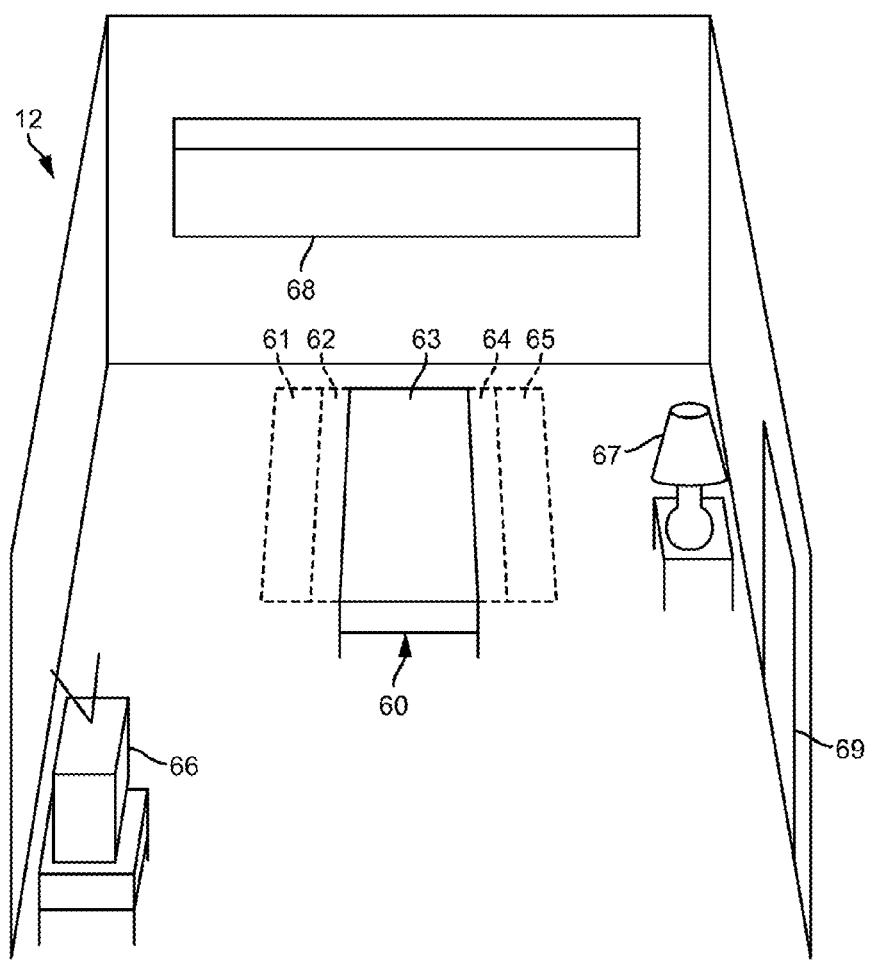
FIG. 4 illustrates a schematic diagram of a patient area according to an embodiment of the present invention.

One or more zones can be defined 52 based on the received 51 user input. For example, one or more zones within and/or outside of a boundary designation can be defined by an algorithm. The one or more zones can correspond with areas of a patient and an IV delivery system, such as areas adjacent to and/or within the bed. In some embodiments, the one or more zones correspond to areas where patient motion is expected. In some cases, a plurality of zones can be defined 52 to cover the bed and/or extend along the bed or other patient area. Various rules can be used by an algorithm of a monitoring system to define 52 the one or more zones. For example, a longitudinal dimension of a zone can be defined 52 as extending parallel with the longitudinal dimension of a bed as indicated by the received 51 input. The zones can be defined 52 in dimensions of pixels. A width dimension of a zone can be defined as extending outward from the boundary designations (e.g., away from the bed) for a predetermined number of pixels. The predetermined number of pixels may correspond with a distance, such as twelve inches. FIG. 4 shows five zones that can be manually or automatically defined 52 based on user input. Specifically, a left outer zone 61, a left inner zone 62, a center zone 63, and right inner zone 64, and a right outer zone 65 are defined 52 along the bed 60.

Referring back to FIG. 3, the method further includes monitoring 53 the defined 52 zones. Motion in the center zone 63 may be indicative of normal patient movement, and motion detected within either of the left inner zone 62 or the right inner zone 64 can indicate that the patient is at least partially off the bed 60. Additionally, motion in the zones may include liquid spills, leaks, expulsion, and dripping, etc. Different rules for monitoring 53 can be applied for the center zone 63 as compared to the inner zones 62 and 64, and the outer zones 61 and 65. Monitoring of the zones can allow particular discrimination algorithms to be run using pixels of thermal images of the zones to identify patterns or other indications of patient events.

Monitoring 53 the one or more patient locations can include separating pixel information indicative of a patient location from pixel information that is irrelevant to a patient location. In some cases, pixels within the defined 52 zones can be assumed to be part of the patient and IV systems as few other features are likely to be outside the zones. Separating the pixel information can include separating the pixels that are within the defined 52 zones from pixels in the frame that are not in the defined 52 zones. Separating the pixels can focus a detection algorithm on the space near and about the bed 60 where the patient is expected to be and can ignore the areas where a patient is not likely to be.

Separating can include distinguishing between those pixels that are within the defined 52 zones from all other pixels of the frame. Pixels within the bed area can be binned for subsequent analysis. Information concerning pixels that are not within defined 52 zones can be deleted or disregarded in subsequent analysis. Separating can include limiting analysis to information for pixels that are within the defined 52 zones to identify a patient location. Only analyzing the information for pixels that are within the defined 52 zones can ease some of the computational burden by not analyzing all of the pixel information from each frame. Also, an algorithm that identifies certain features may be more accurate if it only needs to be capable of assessing the relevancy of pixel information found within a patient area instead of having to assessing the relevancy of all of the different pixel features of the frame.

It is noted, however, that most patient environments are dynamic environments where the arrangement of the bed 60 is frequently changed. For example, a healthcare professional may change an intravenous liquid, and/or provide food, each of which can change the position of the bed 60. Furthermore, the bed 60 and an intravenous system may be wheeled and moved around the patient area 12 by health care professionals when attending to a patient. Some of the changes to the patient area 12 can change the position of the bed 60 relative to one or more heights above the bed. For example, the bed 60 is adjustable and the height of different portions of the bed 60 can change over time. As such, various embodiments of the present disclosure concern techniques for dynamically identifying the surface of the bed 60 (or other patient support surfaces) and setting one or more height thresholds directly above the bed 60 to continuously detect whether a patient is elevating him or herself from the surface of the bed 60. A monitoring system can continue to monitor patient events despite the bed being moved to a different location, lowered, raised, and/or adjusted over time.

Various camera devices and techniques can be employed to perform a scan of a patient area to collect information. Such techniques include infrared thermography (IRT), thermal imaging, and thermal video. For example, thermographic cameras may be used to detect radiation in the infrared range of the electromagnetic spectrum (roughly 900-14,000 nanometers or 0.9-14 µm) and produce thermal images of that radiation. Thermal images may include pixels with color, contrast, and/or intensities dependent on a range of infrared radiation emitted by all objects with a temperature above absolute zero. The amount of radiation emitted by an object increases with temperature and allows one to see variations in temperature. As such, warm objects (e.g., live human body and hot liquids) in a multispectral and/or thermal image stand out well against an environment that is cooler. As a result, thermal images are particularly useful for detecting the presence of liquids.

Part or an entirety of a patient can be identified based on a plurality of pixels within a patient area being grouped together. Identifying the one or more patient locations can include detecting one or more object outlines based on a pixel grouping. Various three dimensional scanning systems can generate point clouds. A point cloud can include a plurality of pixels grouped together, the group representative of the external surface of an object. Each pixel can have coordinates along X, Y, and Z axes. Surfaces can be interpolated between the pixels within the group to generate a three dimensional model of various objects in a scene.

Each grouping of pixel can be built by associating pixels that are proximate each other. For example, two pixels can be grouped if the two pixels are within a predetermined distance from one another (e.g., measured in three dimensional space). Additional pixels can be added to the grouping if each pixel is within a predetermined distance to at least one pixel of the group, within a predetermined distance to multiple pixels of the group, or within a predetermined distance to all pixels of the group, among other options. Because the defined 52 zones have been identified, clusters of pixels within the defined 52 zones are likely to part of a patient. As such, pixel clusters can be indicative of a feature of a patient. Isolated or otherwise ungrouped pixels can be associated with noise and may not be considered to be part of the patient.

Identifying the one or more patient locations can include detecting pixels associated with the patient generally or detecting particular features of a patient, such as a head, chest, arm, leg, and/or other part. Patterns indicative of particular patient features can emerge by recognizing groupings of pixels in a location where a patient feature would be expected (e.g., the head at the top of the bed, arms as the sides of the bed). Particular features of a patient can be detected with templates that correspond to the particular features of the patient. For example, the template can be applied to groupings of pixels to determine whether the profile of a grouping matches a shape of a head, arm, or other patient feature. Identifying the one or more patient locations can include identifying separate locations for different features of a patient, such as the respective locations of the patient's head and arms.

An algorithm can compare pixel characteristics of a zone between sequential frames to determine whether the pixel characteristic of the zone has changed, the change indicative of either patient movement and/or liquid displacement. Patient movement and liquid displacement may be distinguished by features in the infrared, and other spectral planes, images such as thermal or spectral signature and size of moving pixel groups. A thermal signature may include the amount of heat, heat range, heat in certain areas, heat or spectral uniformity and heat or spectral stability of an object. A thermal image characterizes the intensity of the temperature associated with pixels. Spectral images characterize additional characteristics. Temperature can be used for motion detection by identifying changes in the temperature of a zone over time. The temperature of a zone may change over time (e.g., between sequential frames) because the temperature of the surfaces within the zone can change due to introduction of liquids (such as discharges from a human body) within an image.

Referring to FIG. 4, the patient area 12 includes several sources of heat and varied spectral response that can and frustrate accurate detection of patient events and/or cause erroneous detections. For example, turning the television 66 on and off can introduce heat activity into the patient area 12. Furthermore, the television 66 can cause temperature and other spectral fluctuations within the patient area 12 as the screen changes between bright and dark scenes. The lamp 67 or other lighting device can also introduce heat and other spectral activity into the patient area 12. The window 68 can allow outside heat and other spectral radiation into the room. The amount of outside heat and other spectral radiation coming through the window 68 can change due to clouds unpredictably blocking and unblocking direct sunlight, which may affect heat detection. An outside source of heat can come through the doorway 69 to change the temperature and light spectra of the room. Various embodiments of the present disclosure are directed to systems and methods for accounting for such changes in temperature and other spectral responses of the patient area to limit erroneous detections and false alarms. Comparisons between some temperature and other spectral responses-based metric of a zone between frames can determine whether a change in temperature or spectral responses is indicative of a patient event within the zone. For example, the change in temperature or other spectral responses may be compared to a threshold, the threshold distinguishing small changes in temperature or other spectral responses unlikely to be associated with a patient event and larger changes in temperature or other spectral responses likely to be from a patient event. According to another example, a temperature or spectral response change that is at a distance beyond a given threshold from the patient or defined 52 zones may be unrelated to a patient event and may be ignored.

Some systems for monitoring and performing scans of the patient area can include at least one emitter (e.g., laser or infrared based, among other options) and at least one sensor offset from the at least one emitter. Each sensor can be sensitive to the angle at which a reflection of a beam or other projection from the emitter is received after reflecting off of a feature of the scene. The emitter can rapidly scan a scene while the direction and angle of the projection is known at each instance. The angle of reception sensed by the sensor, as well as time of flight, can be determined and the three dimensional coordinates of the reflecting features in the scene can be determined by triangulation or other geometric technique. It is noted that various other techniques for performing three-dimensional scans are possible and are contemplated as within the scope of the present disclosure.

Figure 5:
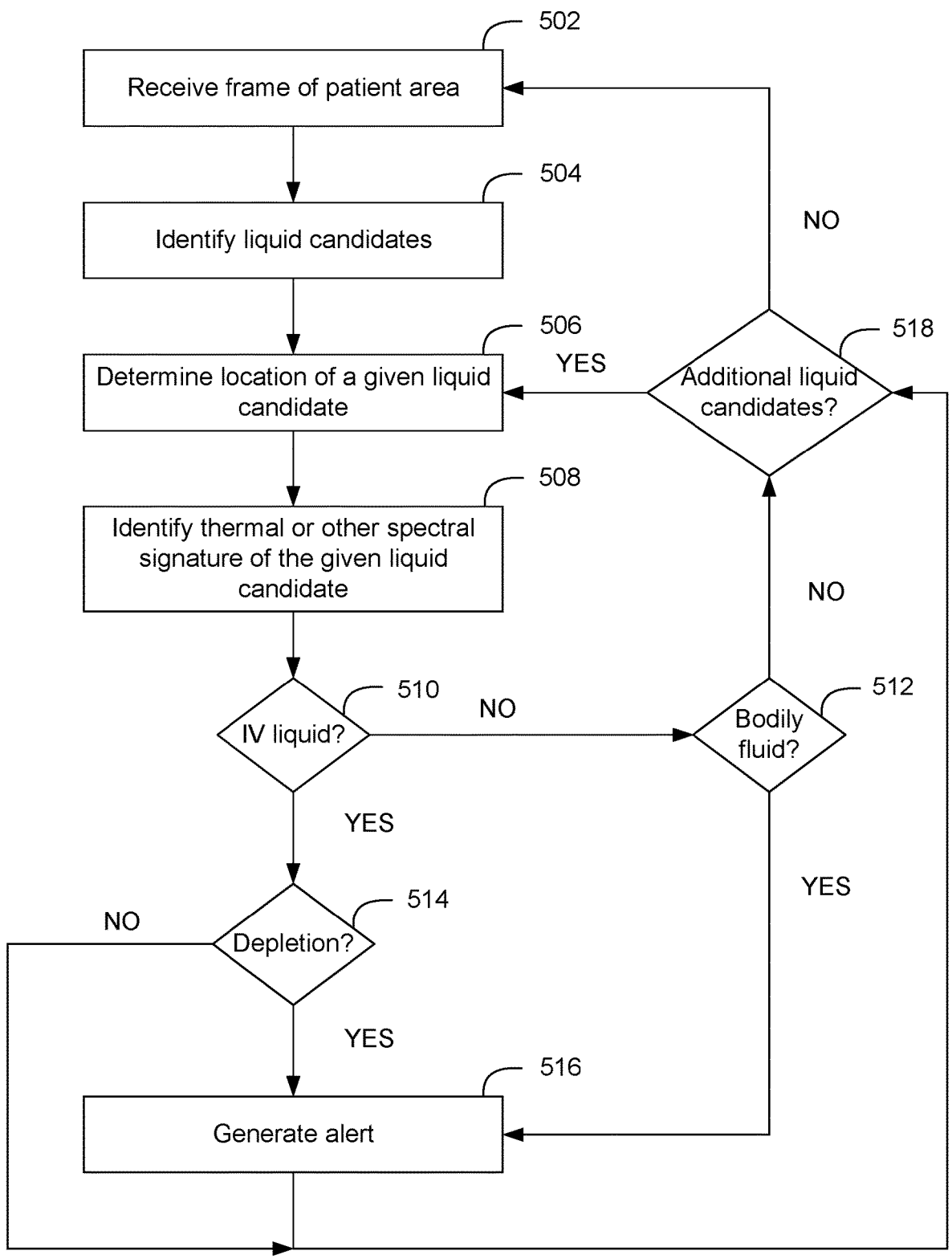
FIG. 5 illustrates a flowchart of a method for detecting liquids according to an embodiment of the present invention.

FIG. 5 shows a flow chart of a method for detecting liquids. The method can be implemented in a monitoring system (e.g., as program instructions) as referenced herein. Some embodiments of the method may be preceded by an initial setup procedure, such as that of FIG. 3. In any case, the method of FIG. 5 includes receiving a frame of patient area, step 502. The frames can be part of a chronological series of frames generated by a camera and transmitted to a computing system in sequence, wherein the steps of the method are performed for the frames of the chronological series. Accordingly, the method steps of FIG. 5 may represent an iteration of a cycle, the cycle being repeated for each frame.

Liquid candidates are identified, step 504. Identifying liquid candidates may include comparing frames of video. A current frame may be compared to a plurality of previously received frames. The current frame may generally refer to the frame most recently received and for which the computing system is processing to detect motion, a change in temperature or spectral response, and/or another event feature. A previous frame may generally refer to a frame that was received previous to the current frame and represents a time that precedes the time represented by the current frame. The current frame can become a previous frame when a next frame (the new current frame) is received and monitoring based on the next frame begins, where the next frame becomes the current frame.

The comparison can include determining a difference between the temperatures, other spectral responses, and/or position of pixels in the current frame and the temperatures and/or position of pixels in the plurality of previous frames. The difference can be determined by subtraction and then optionally taking the absolute value of the result. Based on the difference, the method can identify groups of pixels as liquid candidates. Groups of pixels that exceed or are below certain thresholds may be determined as liquid candidates. The threshold can be set to distinguish between changes in activity due to motion of a thermal or specific object with a specific spectral signature or changes in temperature within a patient area, e.g., a group of pixels not part of the background of a given size smaller than the patient. Groups of pixels may be distinguished from the background via edge detection (or contrast between neighboring pixels), motion detection (by determining specific spectral differences in pixel location from previous frames using either thermal, multispectral or non-thermal imaging, or summing the edges detected within a zone and determining changes in the number of edges within a zone from one frame to the next), and/or having thermal or spectral (multiple or specific) properties different than from the background. The background may be determined as a large group or clusters of pixels having a thermal or spectral property within a given range (e.g., room temperature) and comprising a substantial part of the frame (e.g., greater than 50% of the frame).

Location of a given liquid candidate is determined, step 506. The location of the given liquid may be determined in relationship to the patient area. A thermal or other spectral signature of the given liquid candidate is identified, step 508. Certain liquids may have unique thermal or other spectral signatures associated with them and can be used to identify them. For example, the type of liquid in an IV bag or system may be identified based on unique thermal or spectral signatures. In another example, the type of bodily fluid (e.g., vomit, blood, and urine) may be identified based on their unique thermal or other spectral signatures. The given liquid candidate is determined whether it is IV liquid, step 510. The determination may be made based on the determined location and identified thermal or other spectral signature of the given liquid candidate. For example, IV liquids may be located at a predetermined distance from the patient at certain locations and have uniform temperature or spectral response that is less than or equal to room temperature or having a "normal" spectral response. Additional properties may be considered such as determining (e.g., using at least one of thermal imaging, multispectral or other specific spectral imaging, object detection, motion detection, or any combination thereof) whether the liquid is dripping (drip activity motion) from a stationary reservoir, is depleting, and the presence of an IV line from the liquid candidate to the patient (e.g., detecting a strip of the IV liquid pixels connected to the patient or using edge detection).

If the liquid candidate is determined to be an IV liquid, the method proceeds to determine depletion or a level of depletion of the IV liquid, step 514. Determining depletion may include at least one of: determining a volume of the IV liquid in the current frame, determining volumes of the IV liquid in previous frames, comparing the volume of the IV liquid in the current frame to volumes of the IV liquid in the previous frames, a rate of change in the volume of the IV liquid, and an estimate of when the IV liquid will be depleted. Upon depletion, an alert is generated, step 516. Because the attending HCF staff is charged with caring for several patients in different rooms, the system may actively alert the HCF staff to an patient event (in this case, the depletion of IV liquid), visually and audibly, identifies the patient room by, for example, highlighting a border of a surveillance window and animating alarm icon to draw the attention of the HCF staff to that window and that particular patient room. Additionally, patient event information is prominently displayed within the surveillance window such as a detection of low IV liquids. The system is further operable to recognize replenishment of IV liquids and reset the alarm. Finally, the presently described system and method for using a video monitoring system to detect patient events associated with the presence or lack of liquid provides the HCF staff with a mechanism of rapidly assessing the state of any patient.

Upon generating the alert or if the IV liquid is not depleted, the method determines whether there are additional liquid candidates that were identified, step 518. The presence of additional liquid candidates will return the method to step 506 for analysis of other liquid candidates. Otherwise, the cycle can then be repeated with a next frame of the chronological series at step 502.

In the situation that the liquid candidate is not an IV liquid, the method determines whether the liquid candidate is bodily fluid, step 512. Bodily fluid may be characterized as a warm substance, or that features a specific spectral signature, near, adjacent or surrounding the patient. Bodily fluid may also be determined based on an introduction, flow or movement of a warm object and its dispersion pattern. Examples of bodily fluid dispersion patterns may include expulsion, pooling, accumulation, or leak patterns. If the liquid candidate is not bodily fluid, the method proceeds to determine if there are additional liquid candidates, step 518. In the case that the liquid candidate is bodily fluid, an alert is generated, step 516 and additional liquid candidates are determined afterwards at step 518.

It is noted that the steps of the method of FIG. 5 can be performed in various orders. For example, the steps of the method can be performed in the sequence shown in the flowchart of FIG. 5. However, the steps can be performed in other sequences.

FIGS. 1 through 5 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A system for monitoring a patient in a patient area having one or more detection zones, the system comprising:
   one or more cameras; and
   a computing system configured to:
   receive a chronological series of frames including a plurality of thermal images from the one or more cameras;
   identify liquid candidates by comparing temperature characteristics of a current frame with a plurality of previous frames of the chronological series using edge detection, the comparison based on given pixels of the chronological series of frames including thermal or spectral properties different from thermal or spectral properties of background pixels of the chronological series of frames;
   identify thermal signatures of the liquid candidates;
   determine types of liquids of the liquid candidates based on the thermal signatures of the liquid candidates; and
   generate an alert with the user interface corresponding to the determined types of liquids.

2. The system of claim 1 wherein the computing system is configured to define one or more monitoring zones within a patient area based on input from a user.

3. The system of claim 1 wherein the computing system is configured to detect motion of the liquid candidates by identifying changes in temperature of a given zone between the current frame and the plurality of previous frames.

4. The system of claim 3 wherein the motion includes at least one of liquid spills, leaks, expulsion, pooling, accumulation, and dripping.

5. The system of claim 3 wherein the computing system is configured to detect the motion based on a temperature change corresponding to an appearance of liquids.

6. The system of claim 1 wherein the thermal signatures include an amount of heat, heat range, heat within a given area, heat or spectral uniformity and heat or spectral stability.

7. The system of claim 1 wherein the computing system is configured to identify the liquid candidates based on a comparison to room temperature.

8. The system of claim 1 wherein the computing system is configured to identify the liquid candidates based on a flow or movement corresponding to pixels of a warm object.

9. The system of claim 1, wherein the computing system is configured to determine that the liquid candidates are bodily fluids.

10. A method, in a data processing system comprising a processor and a memory, for monitoring a patient in a patient area having one or more detection zones, the method comprising:
    receiving, by a computing system, a chronological series of frames including a plurality of thermal images from one or more cameras including thermal sensors;
    identifying, by the computing system, liquid candidates by comparing temperature characteristics of a current frame with a plurality of previous frames of the chronological series using edge detection on electronic signals from the thermal sensors, the comparison based on given pixels of the chronological series of frames including thermal or spectral properties different from thermal or spectral properties of background pixels of the chronological series of frames;
    identifying, by the computing system, thermal signatures of the liquid candidates;
    determining, by the computing system, types of liquids of the liquid candidates based on the thermal signatures of the liquid candidates; and
    generating, by the computing system, an alert with the user interface corresponding to the determined types of liquids.

11. The method of claim 10 further comprising defining one or more monitoring zones within a patient area based on input from a user.

12. The method of claim 10 further comprising detecting motion of the liquid candidates by identifying changes in temperature of a given zone between the current frame and the plurality of previous frames.

13. The method of claim 12, wherein the motion includes at least one of liquid spills, leaks, expulsion, pooling, accumulation, and dripping.

14. The method of claim 12 further comprising detecting the motion based on a temperature change corresponding to an appearance of liquids.

15. The method of claim 10 wherein the thermal signatures include an amount of heat, heat range, heat within a given area, heat or spectral uniformity and heat or spectral stability.

16. The method of claim 10 further comprising identifying the liquid candidates based on a comparison to room temperature.

17. The method of claim 10 further comprising identifying the liquid candidates based on a flow or movement corresponding to pixels of a warm object.

18. The method of claim 10 further comprising determining that the liquid candidates are bodily fluids.

* * * * *